US008637037B2

(12) United States Patent
Mistrello et al.

(10) Patent No.: US 8,637,037 B2
(45) Date of Patent: Jan. 28, 2014

(54) ALLERGENS AND ALLERGOIDS FROM BEE VENOM

(75) Inventors: Giovanni Mistrello, Milan (IT); Daniela Roncarolo, Milan (IT); Dario Zanoni, Milan (IT); Paolo Falagiani, Milan (IT)

(73) Assignee: Lofarma S.p.A., Milan (IT)

( * ) Notice: Subject to any disclaimer, the term of this patent is extended or adjusted under 35 U.S.C. 154(b) by 481 days.

(21) Appl. No.: 12/809,503

(22) PCT Filed: Dec. 16, 2008

(86) PCT No.: PCT/IT2008/000767
§ 371 (c)(1),
(2), (4) Date: Aug. 3, 2010

(87) PCT Pub. No.: WO2009/081440
PCT Pub. Date: Jul. 2, 2009

(65) Prior Publication Data
US 2010/0297188 A1    Nov. 25, 2010

(30) Foreign Application Priority Data

Dec. 21, 2007  (IT) .............................. MI2007A2421

(51) Int. Cl.
| *A61K 39/00* | (2006.01) |
| *A61K 39/35* | (2006.01) |
| *A61K 39/36* | (2006.01) |
| *A61K 39/38* | (2006.01) |
| *A23J 1/00* | (2006.01) |
| *C07K 1/00* | (2006.01) |
| *C07K 14/00* | (2006.01) |
| *C07K 16/00* | (2006.01) |
| *C07K 17/00* | (2006.01) |

(52) U.S. Cl.
USPC .................... 424/184.1; 424/276.1; 530/350; 530/412

(58) Field of Classification Search
None
See application file for complete search history.

(56) References Cited

U.S. PATENT DOCUMENTS

2006/0127394 A1   6/2006   Grunwald
2007/0003579 A1   1/2007   Kundig

FOREIGN PATENT DOCUMENTS

| EP | 1 767 543 A1 | 3/2007 |
| WO | WO 2004/081028 A2 | 9/2004 |
| WO | WO 2006/063800 A1 | 6/2006 |
| WO | WO 2007/114575 A1 | 10/2007 |

OTHER PUBLICATIONS

Zurier et al. 'Effect of bee venom on experimental arthritis.' Ann. Rheum. Dis. 32:466-470, 1973.*

Larche et al. 'Immunological mechanisms of allergen-specific immunotherapy.' Nat. Rev. 6:761-771, 2006.*
Kwon et al. 'Water soluble fraction (b10 kDa) from bee venom reduces visceral pain behavior through spinal a2-adrenergic activity in mice.' Pharmacol. Biochem. Behav. 80:181-187, 2005.*
F. Ruëff et al., "Specific Immunotherapy in Honeybee Venom Allergy: A Comparative Study Using Aqueous and Aluminium Hydroxide Adsorbed Preparations." Allergy, vol. 59, pp. 589-595, 2004.
L. Soldatova et al., "Superior Biologic Activity of the Recombinant Bee Venom Allergen Hyaluronidase Expressed in Baculovirus-Infected Insect Cells as Compared with *Escherichia coli*." Journal of Allergy and Clinical Immunology, vol. 101, No. 5, pp. 691-698, May 1, 1998.
F. Kussebi et al., "A Major Allergen Gene-Fusion Protein for Potential Usage in Allergen-Specific Immunotherapy." Journal of Allergy and Clinical Immunology, vol. 115, No. 2, pp. 323-329, Feb. 1, 2005.
S. A. Barker et al., "Separation and Isolation of the Hyaluronidase and Phospholipase Components of Bee Venom and Investigation of Bee Venom-Human Serum Interactions." Toxicon, vol. 4, No. 3, pp. 223, Nov. 1, 1966.
G. Mistrello et al., "Monomeric Chemically Modified Allergens: Immunologic and Physicochemical Characterization." Allergy, vol. 1, No. 51, pp. 8-15, Jan. 1, 1996.
C. Yang et al., "Carbamylation with Cyanate of Basic Phospholipase $A_2$ from the Venom of *Naja nigricollis* (Spitting Cobra)" Toxicon, vol. 19, No. 6, pp. 783-795, Jan. 1, 1981.
G. Passalacqua et al., "Randomised Controlled Trial of Local Allergoid Immunotherapy on Allergic Inflammation in Mite-Induced Rhinoconjunctivitis." The Lancet, vol. 351, No. 9103, pp. 629-632, Feb. 28, 1998.
C. Mollay et al., "Enhancement of Bee Venom Phospholipase $A_2$ Activity by Melittin, Direct Lytic Factor from Cobra Venom and Polymyxin B" FEBS Letters, vol. 46, No. 1-2, pp. 141-144, Sep. 15, 1974.
U. Müller et al., "Type I Skin Reactivity to Native and Recombinant Phospholipase $A_2$ from Honeybee Venom is Similar." Journal of Allergy and Clinical Immunology, vol. 96, No. 3, pp. 395-402, Sep. 1, 1995.
R. Valenta, "The Future of Antigen-Specific Immunotherapy of Allergy." Nature Reviews. Immunology, vol. 2, No. 6, pp. 446-453, Jun. 1, 2002.
D. Marsh et al., "Studies on Allergoids from Naturally Occurring Allergens. III Preparation of Ragweed Pollen Allergoids by Aldehyde Modification in Two Steps." The Journal of Allergy and Clinical Immunology, vol. 68, No. 6, pp. 449-459, Dec. 6, 1981.
R. Asero et al., "Detection of Some Safe Plant-Derived Foods for LTP-Allergic Patients." International Archives of Allergy and Immunology, vol. 144, pp. 57-63, 2007.
P. Falagiani et al., " Specific IgE Density Assay: A New Reverse Enzyme Allergosorbent Test-Based Procedure for the Quantitative Detection of Allergen-Specific IgE." Allergology International, vol. 48, pp. 199-207, 1999.

(Continued)

*Primary Examiner* — Nora Rooney
(74) *Attorney, Agent, or Firm* — Dickstein Shapiro LLP

(57) ABSTRACT

The present invention concerns the preparation of purified allergens and allergoids, both derived from whole bee venom, for the desensitization (immunotherapy) of subjects affected by a specific allergy. In particular, the present invention concerns a preparation for immunotherapy based on purified bee venom, characterized in that said bee venom is essentially mellitin-free. In addition, the preparation of a monomeric allergoid obtainable through the carbamylation or thiocarbamylation reaction of said mellitin-free bee venom, is described. Said allergoid, being characterized by reduced IgE-binding activity, may be a safer and more effective candidate for specific immunotherapy.

12 Claims, 6 Drawing Sheets

(56) References Cited

OTHER PUBLICATIONS

H. Towbin et al., "Electrophoretic Transfer of Proteins from Polyacrylamide Gels to Nitrocellulose Sheets: Procedure and Some Applications." Proc. Natl. Acad. Sci, vol. 76, No. 9, pp. 4350-4354, Sep. 1979.

A. Habeeb, "Determination of Free Amino Groups in Proteins by Trinitrobenzenesulfonic Acid." Analytical Biochemistry, vol. 14, pp. 328-336, 1966.

Flicker et al., "Renaissance of the Blocking Antibody Concept in Type I Allergy." Int. Arch. Allergy Immunol., vol. 132, pp. 13-24, 2003.

U.R. Müller, "Venom immunotherapy: aqueous vs aluminium hydroxide adsorbed extracts"; Allergy, vol. 59, Blackwell Munksgaard, 2004, pp. 577-578.

* cited by examiner

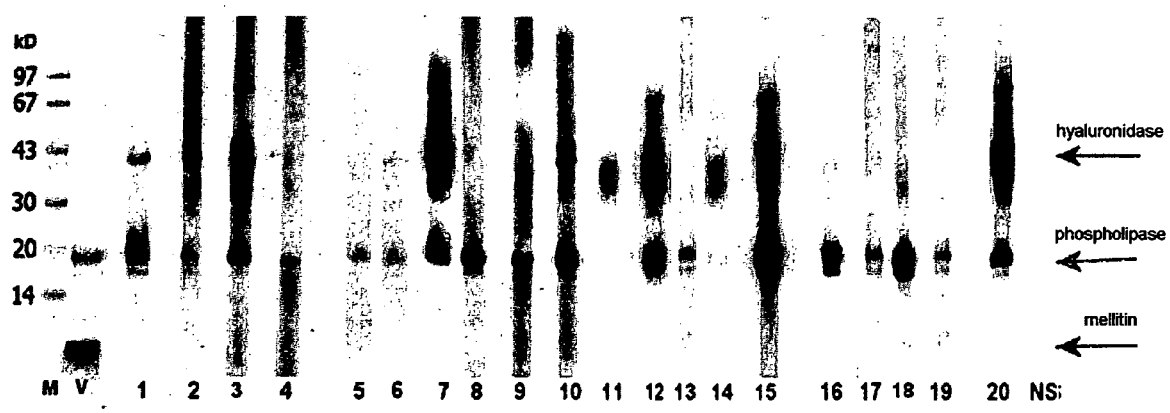
Figure 1. Immunoblotting with serum from bee venom allergic and non-allergic patients
- M: Molecular weight standards
- V SDS-PAGE profile of bee venom dialysed at 3.5 kDa
- 1-20: Sera from patients allergic to bee venom
- NS: Pool of sera from non-allergic subjects Figure 2.SDS-PAGE profile:the effect of duration of dialysis with a membrane with a cut-off of 10 kDa on the elimination of mellitin from bee venom
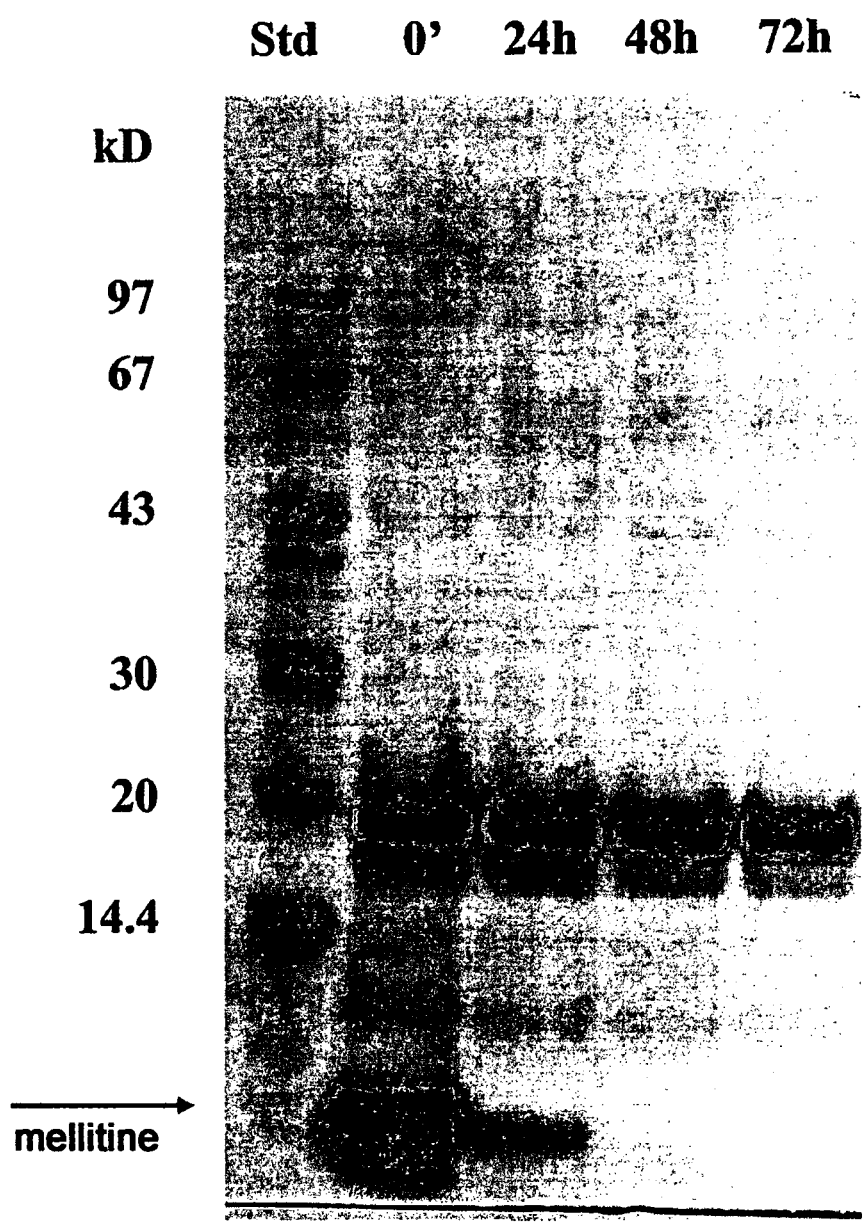

Figure 3. EAST-inhibition determination of IgE reactivity of 10 kDa bee venom and 10 kDa bee venom modified with 0.05 M and 0.5 M potassium cyanate
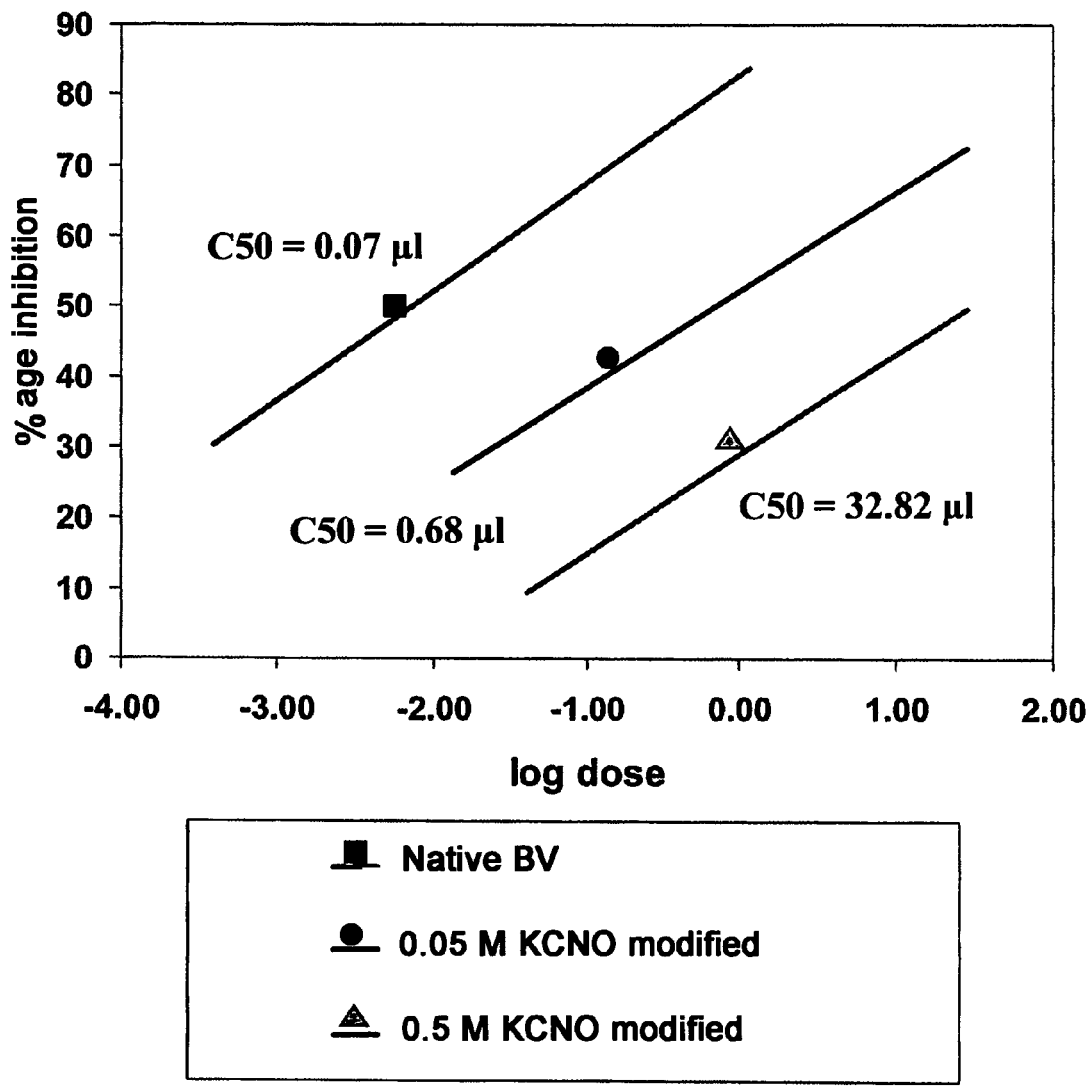
C50: microlitres of sample necessary to obtain 50% inhibition of IgE binding to sphere-bound allergens.

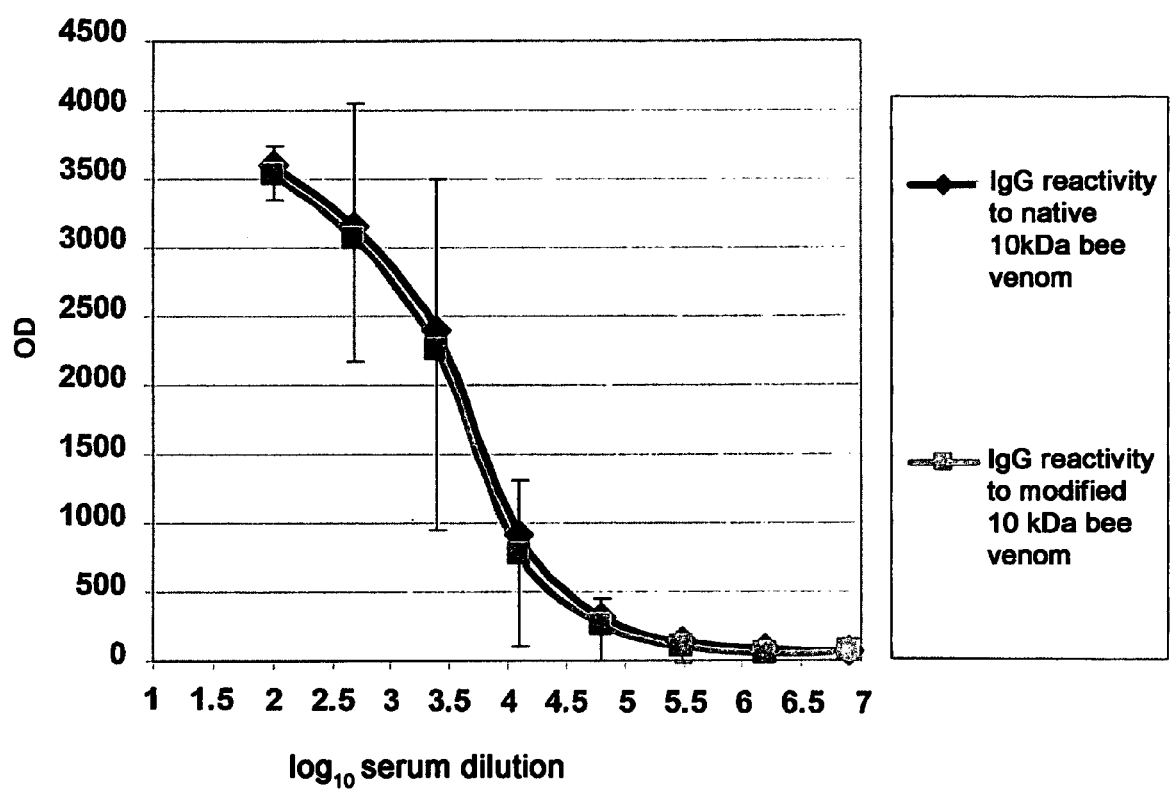
Figure 4. Determination of levels of specific IgE in a pool of sera from mice immunised with modified 10kDa bee venom.

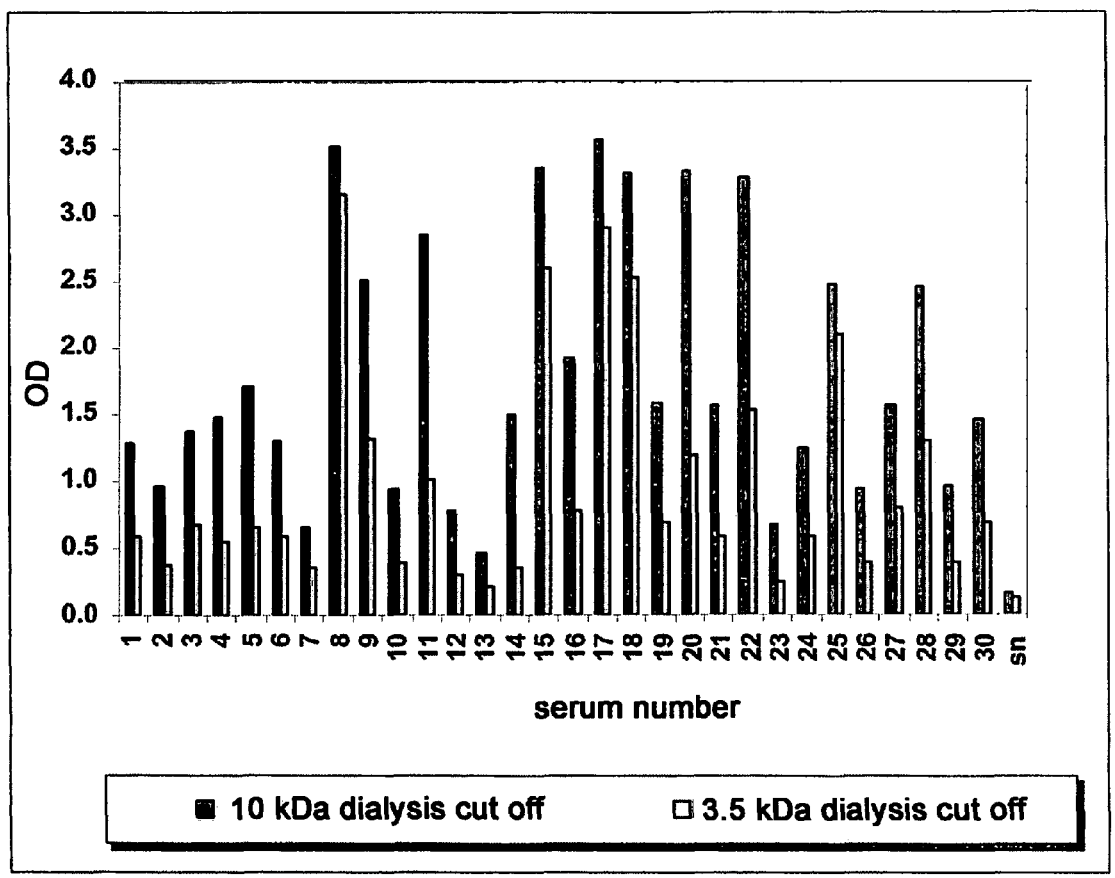
Figure 5. Direct ELISA. Comparison of the IgE reactivity of sera from patients allergic to bee venom against 3.5 kDa or 10 kDa dialysed bee venom.
1-30: sera from patients allergic to bee venom
sn: pool of seras from patients not allergic to bee venom Figure 6. SDS-PAGE profile of native and modified 10 kDa been venom
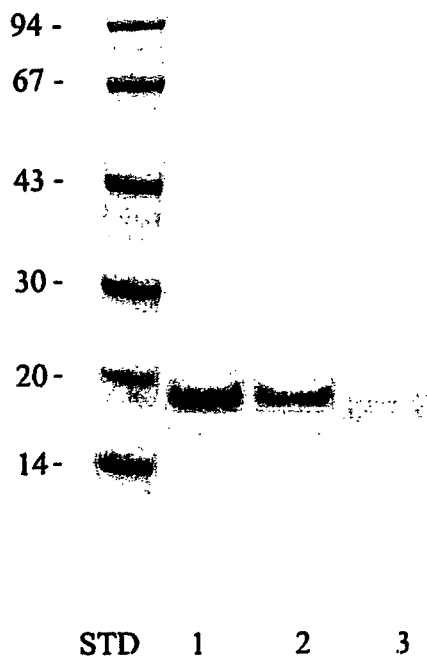
STD Molecular weight standards
1   Native 10 kDa dialysed been venom
2   Bee venom modified using 0.05 M KCNO
3   Bee venom modified using 0.5 M KCNO

ALLERGENS AND ALLERGOIDS FROM BEE VENOM

The present invention concerns allergens purified from bee venom, and allergoids derived therefrom, for the desensitisation (immunotherapy) of subjects affected by a specific allergy.

The incidence of systemic reactions from Hymenoptera stings in the general population is between 0.4 and 5%. Each year, at least 40 deaths are recorded in the USA, 10 in Germany and 5 in Great Britain. Certain particularly exposed categories, such as beekeepers and their families, residents of rural areas and those who, either for work or in the pursuit of hobbies, are involved in open-air activities, are most frequently affected.

Among beekeepers, the prevalence of sensitisation is high, between 15 and 40%, and the risk of allergic reaction is often inversely proportional to the number of stings received per year. It has been shown that subjects with a number of stings per year in excess of 200 have no reactions (a kind of "spontaneous" desensitisation develops), while those with less than 25 stings per year show an incidence of systemic reaction of 45%. The most frequently occurring stings are those caused by bees (*Apis mellifera*) and wasps (*Vespula germanica*); the consequent general systemic symptoms are varied and include facial hot flashes, urticaria, itching, difficult swallowing, difficult breathing (bronchospasm), dizziness, sense of fainting, sweating, pallor, swelling (oedema) affecting the face, eyes, tongue and airways, and may present with varying degrees of severity and with different combinations of symptoms. Swelling and itching are significant symptoms, especially if presenting early (within a few minutes), since they may represent a sign of the imminent onset of a reaction of a certain severity.

The severity of the symptoms also depends on the number of stings the subject receives; in the case of multiple stings (in the order of several tens) the dose of venom injected may even be lethal, due to the toxic effects exerted by the various components present in the venom. It has been calculated that the $LD_{50}$, i.e. the dose required to kill half of a population, is 2.8 mg of venom per kg of body weight of the person stung, for an adult man, and therefore 600 stings might be fatal for a person. Fortunately, the likelihood of being the victim of such a numerous multiple stinging is rare. On the other hand, the risk represented by anaphylactic shock, an event which can lead to the death of an allergic subject as a consequence of even just a single sting, is much more significant and worrying.

In particular, bees sting only once, because their sting, which has small serrations at the end, breaks off from the body when the bee attempts to withdraw it. Thus the insect, having flown away, dies, also leaving the venom sacs containing the venom in the sting site. Only the females are capable of stinging, because, unlike the males, they have stings.

Very often, the victims of such stingings are incapable of identifying the insect that stung them. In such situations, the availability of suitable diagnostic tools is a necessary and essential prerequisite for identifying the species of insect responsible for the allergic reaction. Currently, bee sting allergy may be diagnosed either through the use of in vivo skin prick tests, or through the in vitro determination of serum levels of specific IgE antibodies. Both tests, in turn, envisage the use of special aqueous preparations (extracts) obtained from the venom itself. In individuals with confirmed allergy, the only way to avoid the risk of anaphylactic reaction, which could prove fatal should they be stung again by insects of the same species, is desensitisation therapy or specific immunotherapy (SIT). SIT remains the only form of etiological therapy for allergic pathologies, i.e. capable of interfering with the mechanisms underlying the same and, at the same time, conferring the patient with a specific type of immunological protection, when repeated for a certain number of years (at least three). SIT is based on the administration of increasing doses of the above-mentioned extracts, until reaching the so-called maintenance dose. Unfortunately, although SIT is a therapeutically effective method for allergy to bee venom, it is not without risks and side effects with such a degree of severity as to force the subject to interrupt treatment. For example, undesired reactions of a certain degree have been observed in 15% of patients who have been subjected to increasing doses of bee venom. The causes giving rise to such undesired reactions are still not clear. In the past, numerous studies have been conducted in order to characterise the composition of bee venom, in an attempt to understand the potential causes of this phenomenon.

It has thus been observed that the aforementioned venom consists of a complex mixture of glycoproteins, many of which possessing enzyme activity with digestive action towards tissues, and other components (vasoactive amines, polypeptides, etc.) possessing intrinsic pharmacological effects. However, in allergic subjects, the IgE response is preferentially targeted to only certain of the aforementioned glycoproteins. Of these, phospholipase A2 (PLA2) is the most significant allergen from the clinical viewpoint, since it is recognised by serum IgE in almost all allergic individuals. Even though less important than the phospholipase, other allergens, such as hyaluronidase and acid phosphatase, have been indicated among the high is molecular weight components. Vice versa, with the exception of mellitin, the low molecular weight components (≤3 kDa such as apamine, dopamine, the protease inhibitor, etc.) are incapable of binding IgE and are thus deemed less clinically relevant, or even completely irrelevant. The various enzymes and vasoactive components in venom induce localised inflammation in the area of the sting. A "normal" reaction is represented by a swollen and reddened area of the skin of approx. 10 cm, which can remain that way for several days. By convention, systemic reactions to insect stings are classified in 4 grades, according to Mueller:

grade I. Generalised urticaria, itching, uneasiness, anxiety grade II. Several of the previously mentioned reactions plus two or more of the following: angio-oedema (grade II even if this symptom is present alone), sensation of constriction across the chest, nausea, vomiting, diarrhoea, abdominal pains, dizziness.

grade III. Several of the previously mentioned symptoms, plus two or more of the following: dyspnoea, lack of breath, pulmonary stridor, dysphagia, weakness, aphonia, mental confusion, sensation of impending death.

grade IV. Several of the previously mentioned symptoms, plus two or more of the following: hypotension, cardio-circulatory collapse, loss of consciousness, urinary and foecal incontinence, cyanosis.

For approx. 50 years, an extract prepared from whole bodies has been used for the treatment of bee sting allergies. Around the end of the 1970s, a series of controlled studies demonstrated that extracts prepared from venom sacs, at a maintenance dose of 100 µg of venom protein, were capable of conferring a protective effect in over 80% of patients, and was in any case more effective than SIT based on the use of whole body extract. More recently, it has been observed that treating patients affected by bee sting allergies with "T lymphocytes reactive" peptides derived from phospholipase can induce the same effects (epitope-specific anergy and increased IgG/IgE antibody ratio) observable in patients treated successfully with conventional SIT. This observation, along with numerous others pertaining to other specific allergies, seems to demonstrate that the aforementioned major allergens, predominantly produced in recombinant form, may constitute potential candidates for SIT.

One scope of the present invention is to provide a preparation for desensitisation to bee venom, possessing high tolerance and in particular, minimising the potential undesired effects, without however reducing the desensitising effect of traditional allergen therapy.

The subject of the present invention concerns a preparation obtained by starting from mellitin-free bee venom. This invention is based on the results of a study conducted by the present inventors, where it has been observed that, contrary to current belief, mellitin has no specific effect as an allergen, but can however potentially act as a sensitising agent following prolonged anti-allergy treatment with whole bee venom. The preparation of the invention, mainly consisting of higher molecular weight bee venom components, principally phospholipase A2 (by far and away the clinically most significant allergen) and hyaluronidase, may thus constitute a safer vaccine to be used for SIT in patients allergic to bee venom, or as a diagnostic agent.

Mellitin-free bee venom may be prepared in aqueous form, as described below. For use in SIT, the preparation forming the subject of the invention may be administered parenterally, nasally, sublingually, oromucosally, orally or bronchially, by means of an appropriate administration device. The preparation of the invention may also be obtained in lyophilised form and may then be reconstituted and administered as indicated for the aqueous form, or incorporated into appropriate release systems (e.g. liposomes) or as a powder incorporated in an inert excipient, e.g. lactose, to be administered nasally or bronchially, by means of an appropriate administration device, or made into tablets, possibly for rapid dissolution, for sublingual/oromucosal administration, or capsules, optionally made gastroresistant by means of a suitable procedure, for oral administration.

The preparation of the invention may be administered parenterally, once absorbed or co-precipitated with substances such as L-tyrosine, aluminium hydroxide or calcium phosphate, or with other delay matrices promoting the slow release of the active ingredient from the inoculation site.

The preparation of the invention may also be obtained in the form of an oil suspension, syrup, elixir, with the optional addition of excipients or substances so as to give it a pleasant flavour for sublingual, oromucosal or oral administration.

The preparation of the invention may similarly be associated or mixed with substances known to express Th1 or Treg type adjuvant activity, such as for example CpG, derived from bacteria, mycobacteria, mycoplasmas, *Neisseria*, viruses or protozoa, including non-methylated CpG, lipoproteins or triacylated lipopeptides, polysaccharides and derivatives thereof, also of synthetic origin, synthesised substances such as imiquimod, resiquimod, poly (I:C).

The composition of the invention may generally contain various excipients and/or carriers adapted to the chosen type of administration, in accordance with the knowledge in the possession of those skilled in the art and as reported for example in Remington's Pharmaceutical Sciences Handbook, Mack Pub. Co., N.Y., USA, $17^{th}$ edition, 1985.

In all the above pharmaceutical formulations, the preparation of the invention may be present in quantities comprised of between 0.05 µg (minimum dose) and 50 µg (maintenance dose), in accordance with the typical doses for specific immunotherapy.

The preparation of mellitin-free bee venom may be achieved by means of various methods. The method described herein envisages the dialysis of native bee venom against isotonic saline, using a membrane with a cut-off of 10 kDa, for a period of time sufficient to deplete the venom of mellitin. Generally, a dialysis time of at least 48 hours, more preferably is recommended. Dialysis will preferably be conducted at a temperature comprised of between 0° C. and 10° C.

In any case, removal of the mellitin from the preparation may be achieved by means of other methods, for example by gel-filtration or affinity chromatography with anti-mellitin monoclonal antibodies.

By way of non-limiting example, the present invention will now be described by means of the following preparation example and experimental tests, demonstrating the efficacy of the inventive preparation.

BRIEF DESCRIPTION OF THE FIGURES

FIG. 1: Immunoblotting with serum from patients allergic to bee venom;

FIG. 2: SDS-PAGE profile: Effect of duration of dialysis with a cut-off of 10 kDa on the elimination of mellitin from bee venom;

FIG. 3: Determination of the IgE reactivity of bee venom dialysed with a cut-off of 10 kDa, and the same venom modified with 0.005 M and 0.5 M potassium cyanate, by means of EAST-inhibition;

FIG. 4: Determination of the levels of specific IgG in a pool of serum from mice immunised with bee venom, dialysed with a cut-off of 10 kDa, and modified;

FIG. 5: Direct ELISA; comparison of the IgE reactivity of sera from patients allergic to bee venom vs. venom dialysed with a cut-off of 3.5 kDa or 10 kDa;

FIG. 6: SDS-PAGE profile of native and modified bee venom, dialysed with a cut-off 10 kDa.

EXAMPLE 1

Preparation Procedure for a Mellitin-Free Bee Venom 50 mg of lyophilised bee venom (Latoxan, Valence, France) is dissolved in 10 ml of isotonic saline (0.9% NaCl in distilled water) and left stirring for ten minutes or so. The solution is subsequently passed through a 0.45 µm filter (Puradisc 25 AS, Whatman, Biomap, Agrate Brianza, Milan, Italy) and split into two aliquots of 25 ml each, then subjected to dialysis, one aliquot with a membrane with a cut-off of 3.5 kDa, and the other with a cut-off of 10 kDa (Spectra/Por 7, Spectrumlabs, Prodotti Gianni, Italy). Dialysis is conducted exhaustively against isotonic saline at 4° C., with the aid of a magnetic stirrer, while monitoring the progress of the same by means of SDS-PAGE so as to ascertain the disappearance of the band attributable to mellitin, for the sample subjected to dialysis with the membrane having a cut-off of 10 kDa. Said monitoring may even be achieved using other methods, such as for example, mass spectrometry. Dialysis against isotonic saline for 72 hours may be sufficient, as demonstrated by the SDS-PAGE profile (FIG. 2).

The comparison between the IgE-binding reactivity of bee venom, dialysed using a membrane with a cut-off of 3.5 kDa, compared to a cut off of 10 kDa, i.e. mellitin-depleted, has been conducted using both an in vitro (direct ELISA) method and an in vivo (prick) method, according to the procedures described below.

SDS-PAGE (Method)

Equal quantities (5 μg) of 3.5 kDa bee venom (time 0) and samples of the same subjected to dialysis with a cut-off of 10 kDa (times 24, 48 and 72 hours) are analysed by means of electrophoresis on 10% polyacrylamide gels (pre-cast Nupage Bis-Tris gels, Novex, Prodotti Gianni, Milan, Italy) as described previously (Asero R., Mistrello G. et al. Int. Arch. Allergy Immunol. 2007; 144, 57-63). Electrophoresis is conducted in the specific device (Mighty Small II, Hoefer, Milan, Italy) at 180 mA for 1 hour. The components thus resolved are stained with Coomassie Brilliant Blue (Colloidal Blue staining kit, Amersham, Milan, Italy) and subsequently destained in water. The results shown in FIG. 2 indicate that dialysis for 72 hours allows the more or less complete elimination of the mellitin from the sample.

Direct ELISA

Thirty sera, selected randomly from individuals who, according to REAST (the method is described below), were positive towards bee venom, have been used in the comparison between bee venom dialysed with cut-offs of 3.5 kDa or 10 kDa. To this end, the wells in polystyrene plates have been coated with 0.1 μg (dosage according to BioRad) of bee venom dialysed using a membrane with a cut-off of 10 kDa, or 0.1 μg of bee venom dialysed using a membrane with a cut-off of 3.5 kDa, in 50 mM carbonate/bicarbonate buffer pH 9.6, by incubation at 4° C. for 16 hours. The wells have been washed using wash solution (60 mM phosphate buffer pH 6.5 containing 0.05% Tween-20) and the free sites blocked by incubating with 200 μl of diluent solution (2% BSA, 0.01% Thiomersal in 150 mM phosphate buffer pH 7.4) for one hour at room temperature. Equal volumes (100 μl) of each of the 20 randomly selected human sera are added to each well and then incubated at 25° C. for 2 hours. After washing three times, peroxidase-conjugated rabbit anti-human IgE antiserum (Biospacific, Emeryville, Calif., USA), diluted 1:1500 in diluent solution, is added and incubated at 25° C. for 1.5 hours. After washing three times, development of the colourimetric reaction is obtained by adding 100 μl of TMB reagent (BioFX Laboratories, Owings Mills, Md.) and incubating for 15 minutes at 25° C. The reaction is quenched by the addition of 100 μl of 1 N HCl, and the results evaluated by spectrophotometry at 450 nm (Shimadzu, Mod. UV 1700, Milan, Italy).

The results of the experiments illustrated in FIG. 5 show that the sample of bee venom dialysed using a membrane with a cut-off of 10 kDa maintains, or even shows improved, IgE-binding activity, suggesting that the contribution of mellitin towards the overall IgE-binding activity of bee venom is negligible.

Skin Prick Test on Allergic Patients with Bee Venom Dialysed with a Cut-Off of 3.5 kDa and 10 kDa Eight subjects with a clinical history of allergic reaction to bee venom, and two normal subjects (negative control), have been subjected to skin prick tests, and the two venom solutions (dialysed with a cut-off of 3.5 kDa or 10 kDa), previously diluted 1/50 with prick diluent (0.68% NaCl, 0.275% NaHCO$_3$, 50% glycerol, 0.4% phenol), have been compared. To this end, a drop of solution dialysed with a cut-off of 3.5 kDa is placed on the skin of one forearm prior to pricking the area corresponding to the drop with a special disposable needle, held perpendicular to the surface of the skin. The same operation is then repeated on the skin of the other forearm, after placing a drop of solution dialysed with a cut-off of 10 kDa. A solution of histamine (10 mg/ml) is used as a positive control and diluent solution used as a negative control. For a reaction to be considered positive, the dimensions of the pomphus (weal) must be 3 mm greater than that caused by the diluent solution. On average, for this solution, the skin response has been around 1 mm; in the case of histamine (positive control), the average pomphus dimensions have been 12 mm.

The area of skin involved is inspected after 15-20 minutes, and in the case of a pomphoid reaction, the diameter of the same is traced using a marker pen. The surface of the skin is subsequently covered with a sheet of adhesive paper, thus transferring the outline of the pomphus onto the same. The pomphus is then measured by summing the size of the larger diameter with that of the smaller diameter and dividing by two.

The results are shown in Table 1. This data also confirms that the in vivo allergenic reactivity of the mellitin-free bee venom is entirely comparable to that expressed by mellitin-containing bee venom.

TABLE 1

Skin Prick Test on patients allergic to bee venom with 3.5 kDa and 10 kDa samples

| Patient | Bee venom dialysed with a cut-off of 3.5 kDa Mean pomphus diameter (mm)* | Bee venom dialysed with a cut-off of 10 kDa Mean pomphus diameter (mm)* |
|---|---|---|
| 1 | 5.8 | 5.7 |
| 2 | 4.3 | 4.8 |
| 3 | 5.2 | 5.4 |
| 4 | 6.2 | 5.9 |
| 5 | 4.9 | 5.2 |
| 6 | 5.4 | 5.0 |
| 7 | 4.2 | 4.7 |
| 8 | 4.8 | 5.6 |
| Mean | 5.10 ± 0.69 | 5.28 ± 0.43 |

Both the above results (direct ELISA and skin prick test) suggest that the contribution of mellitin to IgE-binding activity, as determined by both in vitro and in vivo methods, is entirely negligible.

Test to Evaluate the Allergenic Significance of Bee Venom Components

In order to verify the effective clinical significance of the various allergens present in bee venom, we have conducted a series of tests, evaluating the specific. IgE response with regard to the individual allergens easily available on the market, at a high level of purity. The allergens on which we have focussed our attention are mellitin, phospholipase A2 and hyaluronidase.

For the aforementioned tests, 98 sera from patients affected by allergy to bee venom, identified on the basis of a positive skin prick test (SPT), have been subjected to REAST analysis according to the previously described method (Falagiani P, Mistrello G et al. Allergology International 1999, 48:199-20), in order to evaluate the presence of specific IgEs against whole bee venom, phospholipase and mellitin in the serum.

REAST analysis envisages the use of allergens conjugated to biotin according to the process described below.

Preparation of the Biotinylated Allergens 1 mg aliquots of whole bee venom, phospholipase and mellitin (Sigma, Milan, Italy) have been dialysed against 0.1 M NaHCO$_3$ pH 8.4 for 16 hours at 4° C., using a dialysis membrane with a cut-off of 3.5 kDa.

To one side, a solution of N-hydroxy-succinimidyl-biotin (1 mg/ml) in dimethylsulphoxide (DMSO) has been prepared.

454 ml aliquots of this solution are added to the protein to be biotinylated and left to incubate for 4 hours at room temperature, with constant stirring. On completion, unbound biotin is eliminated by dialysis against phosphate buffer.

The working dilution of the purified allergens is determined by conducting a variant of the REAST test, as described below. 50 µl aliquots of pooled serum from patients allergic to bee venom (positive pool) or normal subjects (negative pool) are incubated for 1 hour in the wells of polystyrene plates, to which anti-human IgE serum (0.3 µg/well; Bethyl, Prodotti Gianni, Milan, Italy) has been previously adsorbed. After three washes with wash solution (60 mM phosphate buffer pH 6.5 containing 0.05% Tween-20), 100 µl of serial dilutions (from 1:100 to 1:6400) of the various biotinylated allergens are added to the wells. On completion of a one hour incubation, and three washes with wash buffer, an incubation is conducted with 100 µl of a solution (0.1 µg/ml) of streptavidin-conjugated peroxidase (Pierce, Milan, Italy). After washing three times, development of the colourimetric reaction is obtained by adding 100 µl of TMB reagent (BioFX Laboratories, Owings Mills, Md.) and incubating for 15 minutes at 25° C. The reaction is quenched by the addition of 100 µl of 1 N HCl, and the results evaluated by spectrophotometry at 450 nm (Vmax microplate reader, Molecular Device, Bio-Spa, Milan, Italy).

The working dilution of the various biotinylated allergens will be that which, in the REAST method described below, gives the maximum optical density value for the positive pool associated with an optical density value <0.05 AU for the negative pool.

REAST (Reverse Enzyme Allergo Sorbent Test)

Equal aliquots (50 µl) of 98 sera from patients allergic to bee venom, or a serum of known IgE titre (from 0.5 to 100 kU/l, standard curve), are incubated for 1 hour in the wells of polystyrene plates, onto which anti-human IgE serum (0.3 µg/well) has been previously adsorbed. After three washes with wash solution (60 mM phosphate buffer pH 6.5 containing 0.05% Tween-20), 100 µl of biotinylated bee venom or phospholipase or mellitin, at the previously determined dilutions, are added to the wells relating to the sera under test. While 100 µl of biotinylated anti-human IgE serum are added to the wells pertaining to the standard curve. On completion of a one hour incubation, and three washes with wash buffer, an incubation is conducted with 100 µl of a solution (0.1 µg/ml) of streptavidin-conjugated peroxidase. After washing three times, development of the colourimetric reaction is obtained by adding 100 µl of TMB reagent (BioFX Laboratories, Owings Mills, Md.) and incubating for 15 minutes at 25° C. The reaction is quenched by the addition of 100 µl of 1 N HCl, and the results evaluated by spectrophotometry at 450 nm. The values (in kU/l) of IgEs specific for the three allergens in the test sera, are determined by interpolation of the relevant ODs on the standard curve.

Immunoblotting (IB)

The whole bee venom components, dialysed with a cut-off of 3.5 kDa, are separated by polyacrylamide gel electrophoresis and subsequently transferred onto a nitrocellulose membrane by electroblotting, according to the theory described by Towbin (Towbin J., Staehelin T., Gordon J., (1979): "Electrophoretic transfer of proteins from polyacrylamide gels to nitrocellulose sheets: Procedure and some applications". Proc. Natl. Acad. Sci. USA, 76: 4350-4354).

The membrane is incubated for one hour in TBS-T (TBS, 0.05% Tween-20) containing 5% powdered milk and then overnight with the individual sera from subjects allergic to bee venom (20 selected from those with a specific IgE level >5 kU/l, REAST class 3 or higher), diluted 1:2 in TBS-T, 5% powdered milk. After three washes with TBS-T, the antibodies bound to the membrane are detected by incubating for one hour with peroxidase-conjugated anti-human IgE serum and, after further washes, using the chemiluminescence detection system with reaction with luminol as the peroxidase substrate (ECL, Amersham).

The results of the IB experiments are shown in FIG. 1.

To our great surprise, the aforementioned tests have highlighted that mellitin, a sulphur-free peptide consisting of 26 aminoacids, representing approx. 50% of the dry mass of bee venom, but present in all extracts used for therapeutic purposes to date, in contrast to common conception, is not a clinically significant allergen, by any means. Indeed, in order to be defined as such, an allergen must be recognised, in terms of specific IgE, by at least 60% of the sera from subjects positive for that given substance (in this specific case, bee venom). With regard to the IB profile, it may be observed that phospholipase is recognised by all the sera tested, several of which also recognise hyaluronidase, while mellitin is either not recognised or, even when it is recognised, the corresponding signal is always very weak. Hence, based on our results, mellitin should be considered a rather minor allergen since it is only recognised by a small minority of the sera. In addition, this recognition is always associated with the presence of IgE antibodies specific for other allergens in the serum, foremostly phospholipase A2, the aforementioned IgE response to which is always observed as being much more intense. In terms of kU/l of IgE, mellitin has a mean value of 1.25 (class 1) while the value for phospholipase is 16.9 (class 3).

These results have lead us to believe that mellitin is not a clinically significant allergen, and that precisely for this reason, it may be removed from the preparation, so as to constitute a novel, safer and effective vaccine for treating subjects affected by allergy to bee stings. This product might also be used in SIT in those patients where, having had to interrupt treatment with whole extract due to the onset of undesired reactions, they would be more exposed to the risk of anaphylactic reactions in the case where they were unfortunate to be victims of further bee stings.

The removal of mellitin in the novel extract should also have the advantage of avoiding the risk of sensitising subjects over the course of SIT, since the extracts currently in use contain significant quantities of mellitin and it cannot be excluded that the consequent adverse reactions to the aforementioned SIT are caused precisely by sensitisation to the aforementioned component as a consequence of treatment with the specific vaccine. In order to obtain a further demonstration of the lack of clinical significance of mellitin, a series of additional experiments has been conducted comparing the IgE-binding activity of the venom preparation containing mellitin (following dialysis using a membrane with a cut-off of 3.5 kDa) or without mellitin (following dialysis with a cut-off of 10 kDa). Since a purified form is not available on the market, for the evaluation of the IgE response to hyaluronidase, it has not been possible to conduct either REAST nor direct RAST tests, and so we have referred to the immunoblotting experiments. The presence of hyaluronidase in the sample has been demonstrated by monitoring the specific enzyme activity.

A further scope of the present invention is that of developing another preparation, starting from mellitin-depleted bee venom, in which the major allergens present, represented by phospholipase A2 and hyaluronidase, are chemically modified so as to reduce their IgE-binding reactivity (the risk of side effects is associated with said reactivity), while preserving their immunogenic power (understood as being the capacity to induce specific IgG class antibodies, known to have a protective effect). This may be achieved by submitting the mellitin-depleted bee venom to carbamylation (or thiocarbamylation) reactions, or to reactions forming guanidine type groups on the primary amine groups of the protein portions, particularly on the terminal amino groups and the ϵ-amine residues of lysine. The carbamylation of proteins, a known type of reaction, may effect other aminoacid residues (e.g. the hydroxyl group of tyrosine, the imidazole group of histidine) but all these derivatives are unstable under physiological pH conditions, while the carbamylation reaction products of alpha and epsilon amino groups are very stable.

As demonstrated in the description below, said carbamylate and thiocarbamylate derivatives of mellitin-depleted bee venom, as well as guanidine type derivatives, have shown significantly reduced IgE-binding activity, while, when administered parenterally, their ability to induce specific IgG antibodies capable of also recognising unmodified mellitin-depleted bee venom remains unchanged. Said product may thus represent a safer and effective candidate for SIT in patients with specific allergies.

Hence, an additional subject of the present invention is a preparation containing a modified form of mellitin-depleted bee venom, characterised in that all or a portion of the primary amine groups of the protein components present in the same assume the following structure (I):

(I)

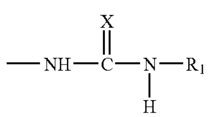

wherein X represents O, S or NR2, where R2 is H, alkyl with 1-6 carbon atoms, phenyl or CN and R1 represents H, alkyl with 1-8 carbon atoms, phenyl or arylalkyl with up to 8 carbon atoms or alkyl containing a heterocyclic ring and that said preparation is water soluble.

The mean percentage of modified primary amine groups must be comprised of between 75% and 100%, preferably around 90%.

Bee venom proteins may be modified according to the invention by treatment with alkaline cyanate (KCNO or NaCNO) or with organic isocyanates or thiocyanates. The reaction must be conducted at a pH comprised of between 7 and 11, preferably between 9 and 9.6, while the temperature in the case of treatment with alkaline cyanate may be comprised of between 20° C. and 50° C., preferably between 35° C. and 40° C., and the reaction time may vary between 12 and 36 hours, preferably between 16 and 24 hours.

In the case of treatment with cyanate, solid KCNO (possibly freshly crystallised) for example may be added, so that the final concentration is between 0.05 M and 1 M, preferably between 0.3 and 0.7 M, more preferably around 0.5 M. The pH of the solution is maintained at the desired value by adding, for example, 0.1 M sodium tetraborate and adjusting the pH by the addition of 1 M NaOH.

In the case of organic isocyanates or isothiocyanates, since in certain cases such compounds are poorly soluble in aqueous environments, the use of a compatible organic solvent may be envisaged.

On completion of the reaction, the mellitin-depleted bee venom thus modified is subjected to gel-filtration in order to eliminate excess reagent and is equilibrated with an appropriate saline solution. Should slight precipitation occur following modification (due to the presence of traces of mellitin, which by reacting with the cyanate, gives rise to an insoluble derivative), this may be removed by appropriate centrifugation.

The chemical modification forming the subject of the present invention may also be performed on purified individual allergens (for example, phospholipase) giving rise to a derivative with the same characteristics as mellitin-depleted bee venom, i.e. reducing IgE-binding activity and maintaining the immunogenic properties.

The degree of substitution of the $NH_2$ groups of the modified, mellitin-depleted bee venom compared to the venom prior to modification, may be determined by means of dosing with trinitro-benzenesulphonic acid (Habeeb, Anal. Bioch. 14, 328, 1966) or by analysing the disappearance of lysine residues and the appearance of homocitrullin by means of appropriate methods known to those skilled in the art.

The chemically modified, mellitin-depleted bee venom according to the procedure described may be prepared in aqueous form and may be administered parenterally, sublingually, oromucosally, orally, nasally or bronchially, the later by means of suitable administration devices. The above described product may also be prepared in lyophilised form and may then be reconstituted and administered as indicated for the aqueous form, or incorporated into release systems (e.g. liposomes) or as a powder, incorporated in an inert excipient, e.g. lactose, to be administered nasally or bronchially, by means of appropriate administration devices, or made into tablets, possibly for rapid dissolution, for sublingual/oromucosal administration, or made into capsules, optionally made gastroresistant by means of a suitable procedure, for oral administration.

The above mentioned product may be administered parenterally, once adsorbed or co-precipitated with substances such as L-tyrosine, aluminium hydroxide or calcium phosphate, or with other "retard" matrices promoting the slow release of the active ingredient from the inoculation site.

The above mentioned product may also be prepared in the form of an oil suspension, syrup, elixir, with the optional addition of excipients or substances so as to give it a pleasant flavour for sublingual, oromucosal or oral administration.

The above mentioned product may similarly be associated or combined with substances known to express Th1 or Treg type adjuvant activity, such as for example CpG, derived from bacteria, mycobacteria, mycoplasmas, *Neisseria*, viruses or protozoa, including non-methylated CpG, lipoproteins or triacylated lipopeptides, polysaccharides and derivatives thereof, also of synthetic origin, synthesised substances such as imiquimod, resiquimod, poly (I:C).

The composition of the invention may generally contain various excipients and/or carriers adapted to the chosen type of administration, in accordance with the knowledge in the possession of those skilled in the art and as reported for example in Remington's Pharmaceutical Sciences Handbook, Mack Pub. Co., N.Y., USA, 17$^{th}$ edition, 1985.

In all the above pharmaceutical formulations, the preparation of the invention may be present in quantities comprised of between 0.1-0.2 μg (initial dose) and 100-200 μg (maintenance dose), according to doses that will thus be generally greater than those typical for specific immunotherapy.

The preparation and the immunogenic activity of the modified mellitin-depleted bee venom according to the invention will now be described by way of non-limiting example.

EXAMPLE 2

Chemical Modification Procedure for a Mellitin-Free Bee Venom 20 ml of mellitin-depleted bee venom (at a concentration of 2 mg/ml), prepared as described in example 1, is subjected to carbamylation by the addition of potassium cyanate and sodium tetraborate decahydrate, in solid form and in such quantities as to give a molarity of 0.05 M or 0.5 M cyanate and 0.1 M tetraborate. The added salts are dissolved by stirring, and the pH adjusted to 9.3 by the addition of 1 M NaOH. The entire mixture is then kept under slow stirring for 18 hours in a thermostatic bath at 40° C. in a suitably sealed container, while monitoring the pH and keeping it constant. On completion of the reaction, the resulting solution is gel-filtered through a column of Sephadex G-25 (Pharmacia, Milan, Italy) in order to eliminate excess cyanate and is equilibrated with isotonic saline, prior to filtration through a 0.22 μm membrane and storage at 4° C. for subsequent tests. Previously, the column has been suitably calibrated in order to collect the excluded peak.

The resulting product has the following characteristics:
- reduced IgE-binding activity, as demonstrated by EAST-Inhibition experiments
- preservation of immunogenic activity, as demonstrated by the ELISA IgG experiments on sera from mice immunised with modified, mellitin-depleted bee venom
- maintenance of the molecular dimensions, as demonstrated by the SDS-PAGE experiments (FIG. 6).

In addition to the aforementioned chemical-biological characteristics, the modified mellitin-depleted bee venom, as described, unexpectedly shows a reduction in the enzyme activities attributable to phospholipase A2 and hyaluronidase, as shown by the agarose gel immunodiffusion experiments (described below), using lecithin and sodium hyaluronate respectively as substrates. This observation may contribute to a further improvement in product safety, since in any case, the aforementioned enzyme components have their own pharmacological activity. As is well known, phospholipase can cause cell membrane damage (cytolysis) and hyaluronidase acts as a "poison diffusion factor" by dissolving hyaluronic acid, a substance present in connective tissue and which binds cells together. Very likely, unlike the IgE-binding activity, the pharmacological effect expressed by phospholipase and hyaluronidase is also inhibited, advantageously conferring the modified product with greater safety. Indeed, the therapeutic effect of bee venom in SIT implies the activation of immunological mechanisms and is thus completely different from the use of the same in anti-inflammatory therapy (bee venom therapy).

Experimental Tests
EAST-Inhibition

For this purpose, glutaraldehyde-activated polystyrene spheres have been coated with bee venom, dialysed with a cut-off of 10 kDa, in an amount of 1 μg per sphere.

In parallel, a pool of human sera is prepared, selected from patients allergic to bee venom, by means of REAST (IgE >20 kU/l).

30 μl of serial dilutions of the test samples (unmodified 10 kDa bee venom, 10 kDa bee venom modified with 0.05 M cyanate and 10 kDa bee venom modified with 0.5 M cyanate) in PBS-2% BSA (diluent) are placed in the wells of an ELISA plate along with 20 μl of serum pool, and the mixture left for 2 hours at room temperature with agitation. In parallel, a positive control sample is prepared where the inhibitor is replaced with diluent. On completion of the two hours, one protein-bound sphere and 50 μl of PBS-2% BSA is added to each well, and agitation of the plate continued overnight at room temperature. The spheres are then washed and 100 μl of a solution of peroxidase-conjugated anti-human IgE antibody added to each well, and the plate incubated with agitation for 2 hours. After washing three times, development of the colourimetric reaction is obtained by adding 100 μl of TMB reagent (BioFX Laboratories, Owings Mills, Md.) and incubating for 15 minutes at 25° C. The reaction is quenched by the addition of 50 μl of 1 N HCl, and 100 μl of mixture from each well transferred to a fresh plate and the colour intensity and evaluated by reading developed spectrophotometrically at 450 nm.

The optical densities measured are transformed into percentage inhibition values with respect to the positive control, and a graph plotted with percentage inhibition on the Y axis, and the $\log_{10}$ of the volume of the sample used in the test on the X axis. From the points reported, a linear regression line is constructed, on which, the $IC_{50}$ value, which represents the volume of sample, in microlitres, necessary to inhibit 50% of IgE binding to the sphere, is measured.

The results, shown in FIG. 3, demonstrate that the addition of suitable concentrations of potassium cyanate to the mellitin-free bee venom solution cause a reduction in the allergenic activity of the venom itself, and in particular, a reduction of approx. 10 fold (0.070 compared to 0.68 μl) for 0.05 M cyanate and approx. 500 fold (0.070 compared to 32.82 μl) for 0.5 M cyanate.

Mouse Immunisation Protocol

A group of mice, consisting of four Balb/c females (Charles River) is immunised, subcutaneously, with 200 μl of an emulsion consisting of 100 μl of Freund's complete adjuvant and 20 μg of mellitin-depleted bee venom, modified with 0.5 M KCNO following dialysis with a 10 KDa cut-off, in 100 μl of isotonic saline. A further three booster injections are conducted at two weekly intervals, with incomplete adjuvant in place of complete. Seven days after the final immunisation, blood is taken from the tails of the mice and the specific IgG response with regard to the immunogen (modified mellitin-depleted bee venom) checked by ELISA, just as the capacity to recognise wild-type protein (mellitin-depleted bee venom).

IgG ELISA of Sera from Mice Immunised with Modified Mellitin-Depleted Bee Venom

Equal quantities (0.25 μg) of mellitin-depleted bee venom or modified mellitin-depleted bee venom, in 50 mM carbonate/bicarbonate buffer pH 9.6, are adsorbed onto the wells of polystyrene ELISA assay plates by incubation at 4° C. for 16 hours. The wells are then washed with wash solution (60 mM phosphate buffer pH 6.5 containing 0.05% Tween-20) and the free sites blocked with diluent solution (25% horse serum, 1 mM EDTA, 0.05% Tween 20, 0.01% Thiomersal in 150 mM phosphate buffer pH 7.4). Equal aliquots (100 μl) of serial dilutions of serum from each mouse in diluent buffer are added to each well and left to incubate at 25° C. for 2 hours. After three washes and the addition of peroxidase-conjugated anti-mouse IgG serum, diluted 1:2000 in diluent buffer, incubation is continued at 25° C. for 1.5 hours. After washing three times, development of the colourimetric reaction is to obtained by adding 100 μl of TMB reagent (BioFX Laboratories, Owings Mills, Md.) and incubating for 15 minutes at 25° C. The reaction is quenched by the addition of 100 μl of 1 N HCl, and the results evaluated by spectrophotometry at 450 nm.

FIG. 4 shows the IgG reactivity of the sera from animals immunised with bee venom modified with 0.5 M cyanate with regard to the native or cyanate-modified mellitin-depleted bee venom proteins.

The fact that the IgG response of said sera is targeted not only to the modified venom (mellitin-depleted) but is also capable of recognising native venom (mellitin-depleted), i.e. unmodified venom, demonstrates that the immunogenic capacity of the modified venom is more or less unchanged. This is extremely important from a therapeutic perspective, since the induction of specific IgG is considered a determining factor in the expression of SIT clinical efficacy (Flicker S, Valenta R.; *Int. Arch. Allergy Immunol.* 2003; 132(1):13-24).

SDS-PAGE

Equal quantities (5 mg) of bee venom dialysed using a membrane with a cut-off of 10 kDa and samples of the same subjected to chemical modification with 0.05 or 0.5 M cyanate are analysed by means of electrophoresis on 10% polyacrylamide gels (pre-cast Nupage Bis-Tris gels, Novex, Prodotti Gianni, Milan, Italy) as described previously (Asero R., Mistrello G. et al. *Int. Arch. Allergy Immunol.* 2007; 144, 57-63). Electrophoresis is conducted in the specific device (Mighty Small II, Hoefer, Milan, Italy) at 180 mA for 1 hour. The components thus resolved are stained with Coomassie Brilliant Blue (Colloidal Blue staining kit, Amersham, Milan, Italy) and subsequently de-stained in water. The results shown in FIG. 6 clearly indicate that the chemical modification process used has not significantly altered the molecular dimensions of the components present. This final element is extremely important for the use of the product for therapeutic ends, especially in the case of administration of the same sublingually/oromucosally.

Enzyme Activity Measurement of the Phospholipase A2 Allergen

The presence and quantification of phospholipase A2 (PLA2) in the bee venom has been highlighted by analysing its enzyme activity in an agarose gel containing the enzyme's natural substrate (lecithin).

For this end, 50 ml of a 2% solution of agarose in 40 mM Tris pH 8, 0.1% $NaN_3$, has been prepared. After having dissolved the agarose by boiling the solution and having subsequently cooled it to approx. 56° C., it is added with 50 ml of a 3% emulsion of soya phosphatidyl choline (soya lecithin, Sigma, Milan) in the same buffer. Finally, after having added 1 ml of 10 mM $CaCl_2$, and having distributed 15 ml of the mixture in 100 mm diameter Petri dishes and having left them to cool until the gel has solidified, the plates are allowed to rest at 4° C. overnight. Subsequently, wells with a diameter of approx. 4 mm have been made in the gel and the solutions to be analysed, native or modified PLA2 standard (500, 20 and 1 U/ml) or native or modified bee venom (with 0.05 M or 0.5 M KCNO) in 1 M NaCl, 0.1% BSA, 0.1% $NaN_3$ have been prepared.

After pipetting 10 μl of each solution into the wells (with each sample being analysed in duplicate), the plates have been placed in a humidified incubator at 37° C. for approx. 20 hours. Finally, the enzyme activity has been analysed by measuring the diameter of the translucent halos that form around the wells due to hydrolysis of the lecithin. The size of each halo is directly proportional to the enzyme activity present in the sample. Halo sizes for the various concentrations of phospholipase standard have allowed a standard curve to be plotted, from which the values obtained for the test samples may be extrapolated. From this analysis, it is evident that the bee venom dialysed with a cut-off of 10 kDa had a phospholipase concentration of 76 U/mg of lyophilised venom; following modification with 0.05 M or 0.5 M KCNO, this activity dropped to 57 and 0.8 U/mg respectively.

Enzyme Activity Measurement of the Hyaluronidase Allergen

The presence and quantification hyaluronidase in the bee venom has been highlighted by analysing its enzyme activity in an agarose gel containing the enzyme's natural substrate (hyaluronic acid or sodium hyaluronate).

For this end, 50 ml of a solution of sodium hyaluronate in 0.1 M citrate/NaCl buffer pH 5.3 and, in parallel, 10 ml of a 3% solution of agarose in the same buffer, have been prepared. After having dissolved the agarose by boiling the solution and after having subsequently cooled it to approx. 60° C., the two solutions have been mixed and the mixture distributed in 100 mm diameter Petri dishes. After cooling at room temperature until the gel has solidified, the plates are allowed to rest at 4° C. for 2 hours. Subsequently, wells with a diameter of 4 mm have been made in the gel and the solutions to be analysed, hyaluronidase standard (1000, 500 and 250 U/ml) or native mellitin-depleted bee venom or venom modified with 0.5 M KCNO have been prepared (both of the latter at 50 μg/ml)

After pipetting 10 μl of each solution into the wells (with each sample being analysed in duplicate), the plates have been placed in a humidified incubator at 37° C. for approx. 20 hours. Finally, the enzyme activity has been visualised by pouring 30 ml of 10% cetylpyridinium in $H_2O$ per plate over the gel, and analysed by measuring the diameter of the transparent halo that forms around the wells against the opaque background of the plate. The size of each halo is directly proportional to the enzyme activity present in the sample. Halo sizes for the various concentrations of hyaluronidase standard have allowed a standard curve to be plotted, from which the values obtained for the test samples may be extrapolated. From this analysis, it is evident that the bee venom dialysed using a membrane with a cut-off of 10 kDa had a hyaluronidase concentration of 9550 U/mg of lyophilised venom; while, following modification with 0.5 M KCNO, said activity was no longer detectable.

Conclusion

The product derived (referred to as monomeric allergoid in order to distinguish it from other allergoids, obtained by reaction with aldehydes, formaldehyde or glutaraldehyde, wherein the components assume considerably greater molecular dimensions, resulting in the name of polymer type) may represent the ideal candidate for SIT with a specific vaccine to be administered, even by routes other than parenterally.

The aim of the modification is to reduce the IgE-binding activity (to which the risk of adverse reactions is associated) and to preserve the immunogenic capacity (understood as the capacity to induce IgG antibodies with which the possibility of clinical benefit is associated) of the safer bee venom preparation to be used in SIT in patients allergic to bee venom. The reduced enzyme activity of the monomeric allergoid compared to unmodified allergen increases its safety of use.

The invention claimed is:

1. A preparation for bee venom based immunotherapy, wherein said preparation comprises bee venom which is essentially mellitin-free and consists of components with a molecular mass greater than 10 kDa, wherein said bee venom which is essentially mellitin-free is obtained by dialysis of native bee venom using a membrane with a cut-off of 10 kDa, and wherein at least one primary amine group located on at least one protein portion of said bee venom which is essentially mellitin-free is subjected to carbamylation or thiocarbamylation or to the formation of guanidine type groups so as to form monomeric allergoids.

2. The preparation according to claim 1, wherein said primary amine groups are terminal amino groups and/or the ε-amino residues of lysine.

3. The preparation according to claim 1, wherein all or part of the at least one primary amine group of the protein portion of said bee venom which is essentially mellitin-free assumes the following structure (I):

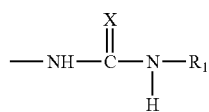

wherein X represents O, S or NR2, where R2 is H, alkyl with 1-6 carbon atoms, phenyl or CN and R1 represents H, alkyl with 1-8 carbon atoms, phenyl or arylalkyl with up to 8 carbon atoms or alkyl containing a heterocyclic ring.

4. The preparation according to claim 3, said preparation being water soluble.

5. The preparation according to claim 3, wherein the mean percentage of modified primary amine groups is greater than 75%.

6. The preparation according to claim 5, wherein the mean percentage of modified primary amine groups is approx. 90%.

7. The preparation according to claim 1, obtainable by treatment of said mellitin-depleted bee venom with an alkaline cyanate such as KCNO or NaCNO or with organic isocyanates or isothiocyanates at a pH comprised of between 7 and 11.

8. The preparation according to claim 7, said treatment being conducted at a pH comprised of between 9 and 9.6.

9. The preparation according to claim 7, said treatment being conducted with alkaline cyanate at a temperature comprised of between 20° C. and 50° C., or between 35° C. and 40° C. and for a reaction time varying between 12 and 36 hours, or between 16 and 24 hours.

10. The preparation according to claim 7, said treatment being conducted with solid KCNO in such a manner that the final concentration is between 0.05 M and 1 M, or between 0.3 and 0.7 M, or approx. 0.5 M.

11. The preparation according to claim 7, wherein, on completion of the reaction, the mellitin-depleted bee venom thus modified is subjected to gel-filtration in order to eliminate excess reagent and is equilibrated with an appropriate saline solution.

12. A pharmaceutical composition comprising an immunotherapeutically efficacious dose of the preparation according to claim 1, together with pharmaceutically acceptable excipients.

* * * * *

UNITED STATES PATENT AND TRADEMARK OFFICE
CERTIFICATE OF CORRECTION

PATENT NO.       : 8,637,037 B2                                              Page 1 of 1
APPLICATION NO. : 12/809503
DATED            : January 28, 2014
INVENTOR(S)      : Mistrello et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 524 days.

Signed and Sealed this
Twenty-second Day of September, 2015

Michelle K. Lee
*Director of the United States Patent and Trademark Office*